United States Patent
Redel

(10) Patent No.: US 10,157,490 B2
(45) Date of Patent: Dec. 18, 2018

(54) ANGULATION PLANNING FOR A THREE DIMENSIONAL ANGIOGRAPHY

(71) Applicant: Thomas Redel, Poxdorf (DE)

(72) Inventor: Thomas Redel, Poxdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/685,786

(22) Filed: Aug. 24, 2017

(65) Prior Publication Data
US 2018/0061114 A1    Mar. 1, 2018

(30) Foreign Application Priority Data
Aug. 25, 2016    (DE) .......................... 10 2016 215 970

(51) Int. Cl.
*G06K 9/00* (2006.01)
*G06T 15/08* (2011.01)
(Continued)

(52) U.S. Cl.
CPC .............. *G06T 15/08* (2013.01); *A61B 6/032* (2013.01); *A61B 6/504* (2013.01); *A61B 6/5241* (2013.01);
(Continued)

(58) Field of Classification Search
USPC ................................................ 382/128–134
See application file for complete search history.

(56) References Cited

U.S. PATENT DOCUMENTS

2004/0066958 A1*    4/2004    Chen ...................... A61B 6/466
                                                                       382/128
2007/0036264 A1    2/2007    Beyrard
(Continued)

FOREIGN PATENT DOCUMENTS

CN           101991427 A        3/2011
DE      102006011242 A1        9/2007
(Continued)

OTHER PUBLICATIONS

German Grant Decision for related German Application No. 10 2016 215 970.4 dated Aug. 26, 2016.
(Continued)

*Primary Examiner* — Alex Kok S Liew
(74) *Attorney, Agent, or Firm* — Lempia Summerfield Katz LLC

(57) ABSTRACT

A method and system for operating an x-ray device for a creation of a three-dimensional angiography of a body vessel segment. A three-dimensional reconstruction of the body vessel segment is provided to a computing device of the x-ray device. A center line of the body vessel segment is computed. An axis of rotation is laid through the center line. The three-dimensional reconstruction is registered with the x-ray device. The suitability of at least one recording angle pair with a first and a second recording angle for the creation of the three-dimensional angiography is assessed on the basis of an assessment criterion by the computing device. One of the at least one assessed recording angle pairs is selected for creation of the three-dimensional angiography as a function of a result of the assessment, in order to improve the creation of the three-dimensional angiography.

20 Claims, 2 Drawing Sheets

(51) Int. Cl.
   *A61B 90/00*  (2016.01)
   *A61B 6/03*   (2006.01)
   *A61B 6/00*   (2006.01)
   *G06T 7/33*   (2017.01)

(52) U.S. Cl.
   CPC .............. *A61B 90/00* (2016.02); *A61B 90/36* (2016.02); *G06T 7/337* (2017.01); *A61B 2090/367* (2016.02); *G06T 2207/10116* (2013.01); *G06T 2207/20224* (2013.01); *G06T 2207/30048* (2013.01); *G06T 2207/30101* (2013.01)

(56) References Cited

U.S. PATENT DOCUMENTS

| | | | |
|---|---|---|---|
| 2007/0232886 | A1 | 10/2007 | Camus et al. |
| 2010/0008557 | A1* | 1/2010 | Matsumoto ........ G06K 9/00208 382/131 |
| 2011/0044525 | A1 | 2/2011 | Ohishi |
| 2015/0356753 | A1 | 12/2015 | Lauritsch et al. |

FOREIGN PATENT DOCUMENTS

| | | |
|---|---|---|
| DE | 102014210591 A1 | 12/2015 |
| WO | WO2007006560 A2 | 1/2007 |

OTHER PUBLICATIONS

German Office Action for related German Application No. 10 2016 215 970.4 dated Mar. 3, 2017.

Morris, Paul D. et al.: "Virtual" (Computed) Fractional Flow Reserve, in: JACC: Cardiovascular Interventions, vol. 8, No. 8, 2015, pp. 1009-1017; ISSN:1936-8798; DOI:10.1016/j.jcin.2015.04.006.

German Grant Decision for related German Application No. 10 2016 215 970.4 dated Aug. 26, 2016, with English Translation.

German Office Action for related German Application No. 10 2016 215 970.4 dated Mar. 3, 2017, with English Translation.

European Search Report for European Patent Application No. 17184248.7-1124, dated Jan. 29, 2018.

Chinese Office Action for Chinese Application No. 201710740448.0, dated Sep. 12, 2018, with English Translation.

\* cited by examiner

ANGULATION PLANNING FOR A THREE DIMENSIONAL ANGIOGRAPHY

CROSS REFERENCE TO RELATED APPLICATIONS

This application claims the benefit of DE 102016215970.4 filed on Aug. 25, 2016 which is hereby incorporated by reference in its entirety.

FIELD

Embodiments relate to a method for operating an x-ray device for creating a three-dimensional angiography of a body vessel segment or body vessel.

BACKGROUND

An established clinical characteristic variable is the Fractional Flow Reserve (FFR). The FFR may be measured with a pressure wire for example. The pressure wire is guided past a stenosis in the body vessel or body vessel segment and determines the pressure there distal to the stenosis. The distal pressure is divided by the proximal pressure in order to calculate the fractional flow reserve.

With a three-dimensional model of the body vessel segment or body vessel section in which the stenosis is contained, and further boundary conditions, such as for example the blood flow in milliliters per second through the body vessel segment, the pressure curve via the stenosis may be calculated using mathematical methods of fluid dynamics (computational fluid dynamics). A virtual value may be computed for the fractional flow reserve, a virtual FFR value, virtually on the basis of the three-dimensional model. Methods are described, for example, in the article by Paul D. MORRIS et al.: ""Virtual" (Computed) Fractional Flow Reserve—Current Challenges and Limitations" in JACC: Cardiovascular Interventions, Vol. 8, No. 8, 2015, pages 1009 to 1117. Other methods of computation for a virtual FFR value are also known.

The approaches to virtual computation of the fractional flow reserve may be divided up into two groups. Non-invasive methods, in which geometry information about the body vessel segment or body vessel is obtained by computed tomography, magnetic resonance tomography or other methods, and minimally invasive methods, in which the geometry information is obtained in the cardiac catheter laboratory by an injection of contrast medium into the vessel with a subsequent x-ray recording. A non-invasive examination of a patient is initially undertaken by computed tomography (CT). As well as the diagnostic information about one or more vessel cross sections of the examined body vessel segment or body vessel, a virtual value for the fractional flow reserve may also be computed that is referred to as the CT FFR value. By contrast, a virtual value for a fractional flow reserve, that is established by an angiography in the cardiac catheter laboratory for example, will be referred to as an angio FFR value.

The CT FFR method, e.g. the computation of the virtual FFR value by CT, includes a three-dimensional model of the entire vascular tree in which the body vessel or the body vessel segment with the stenosis is located, is available. The CT FFR method allows for a good determination of the perfused myocardial mass as well as of the perfusion flow derived from the proportion of the perfused myocardial mass. Furthermore additional information, such as for example a composition of the stenosis or of the plaque, may be established. The disadvantage is the comparatively low spatial resolution and thus an imprecise geometry representation of the stenosis geometry.

By comparison, the angio FFR method, e.g. the computation of a virtual FFR value using an angiography, includes good spatial resolution, that makes a precise representation of the stenosis geometry possible. A disadvantage is the estimation of the blood flow via the vessel cross sections. Even small errors may result in large effects. The estimation of the blood flow via contrast media dynamics is complex and difficult in the angio FFR method. A further disadvantage is that the angio FFR method does not deliver any information about a state of the myocardial mass, that is important for example for recognizing any possible prior damage and enabling it to be taken into account during a treatment. Geometry information of the vascular tree as a whole may only be obtained with great difficulty, that is also attributable to the relatively small detectors used in angiographies.

SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide an improvement for a creation of a three-dimensional angiography, so that an FFR value may be established more quickly and more accurately.

Embodiments relate to a method for operating an x-ray device for a creation of a three-dimensional angiography of a body vessel segment or body vessel with a series of acts. In an example, the body vessel or body vessel segment may be a coronary or a segment of a coronary.

A three-dimensional reconstruction is provided at a computing device of the x-ray device of the body vessel segment or of the body vessel that was recorded by another imaging device, for example, an x-ray device such as a computed tomography device or a magnetic resonance tomography device. The three-dimensional reconstruction may be effected in the form of a registration dataset, that for example includes data about the three-dimensional model, for example, with image data and/or segmentation data and/or center line data and/or other feature data for computing a CT FFR value. The body vessel segment or body vessel may include a coronary vessel or a coronary vessel segment. The body vessel segment or body vessel may include a diseased body vessel segment or body vessel. For example, the body vessel segment or body vessel may include a stenosis.

If a three-dimensional reconstruction of the body vessel is provided, the body vessel segment of the body vessel may be marked in the three-dimensional reconstruction. The marking may be effected by an operator. The marked or provided body vessel segment may include a body vessel segment of the body vessel in which a stenosis is present, or other, for example, undesired, deposits or changes are present.

A center line may be computed through the body vessel segment or through the marked body vessel segment and a laying of an axis of rotation through the center line. Both the computation and the laying of the axis of rotation are effected by the computing device of the x-ray device. The center line follows a course of the body vessel segment along a center of the body vessel segment and, for example, a blood flow through the body vessel segment. The axis of rotation, as a straight line, may approximate to the center line for example such that an error between center line and axis of rotation, for example an inverse square, is minimized.

The center line may be computed locally in a predetermined region, for example, the region of the detected stenosis. The center line may be effected in an already segmented three-dimensional reconstruction of the body vessel segment, but also on image data. At least one local segmentation in the region of the body vessel segment or marked body vessel segment, e.g. the stenosis, is necessary. A segmentation may be understood as the assignment of a pixel or of a voxel to a part of the body.

The three-dimensional reconstruction is registered with the x-ray device. The registration dataset of the three-dimensional reconstruction may be registered with a planning dataset of the body vessel or body vessel segment recorded by the x-ray device. The registration is to be understood here in the sense of an image registration, in which the three-dimensional reconstruction is placed in a defined, uniquely-determined spatial relationship to the x-ray device or to the registration dataset with the planning dataset respectively, in order to bring the body vessel or body vessel segment in the three-dimensional reconstruction into a spatial match with the body vessel segment or body vessel in the recorded planning dataset or in the x-ray device. Methods for automatic or semi-automatic image registration in three dimensions or two dimensions as well as mixtures of two-dimensional and three-dimensional data are known. The x-ray device or parts of the x-ray device, such as a recording unit for example, is brought into a predetermined spatial relationship with the (e.g. marked) body vessel segment of the three-dimensional reconstruction.

The suitability of at least one recording angle pair is assessed with a first and a second recording angle for the creation of the three-dimensional angiography on the basis of an assessment criterion by the computing device. The assessment may involve one or more recording angle pairs. The assessment may also be carried out repeatedly. The assessment of the suitability of a recording angle pair may also inherently include the assessment of the suitability of the first and/or the second recording angle. The assessment of the suitability of a recording angle pair may, for example, also be an assessment of a first and a second recording angle in mutual dependency.

The three-dimensional angiography is created with a first recording of the body vessel or body vessel segment by the x-ray device from the first recording angle and a second recording of the body vessel by the x-ray device from the second recording angle. The assessed recording angles may be perpendicular to the axis of rotation. The term perpendicular also includes "substantially perpendicular", e.g. a deviation from the right angle by a few degrees, for example by fewer than 15°, fewer than 10° or fewer than 5°. The three-dimensional angiography is created with especially high accuracy. The recording angles or recording angle pairs that are assessed may be pre-selected at random. All recording angles or recording angle pairs, for example, all recording angles or recording angle pairs accessible to the x-ray device, that are perpendicular to the axis of rotation, may be assessed.

One of the at least one assessed recording angle pairs, e.g. of the assessed recording angle pair or of one of the assessed recording angle pairs, is selected for creation of the three-dimensional angiography. The selection is made as a function of a result of the assessment. The recording angle pair that achieved the best result during the assessment may be selected. The recording angle pair may also be selected step-by-step. For example, there may first be a selection of the first recording angle and then, as a function of the selected first recording angle, a second recording angle may be selected. The second recording angle may also be assessed separately from the first recording angle and may be assessed after the selection of the first recording angle. There may also be provision for only selecting a recording angle pair or the recording angle pair if the result of the assessment achieves a predetermined minimum result, for example a predetermined minimum quality, e.g. if only one recording angle pair is assessed.

The information already available about the body vessel or body vessel segment, that is contained in the three-dimensional reconstruction of the body vessel segment or body vessel, is used for the planning of the three-dimensional angiography or of the angles or angulations used for the three-dimensional angiography, in order to achieve an angiography with improved quality compared to known methods and to achieve more precise values for a virtual FFR value, that is computed on the basis of the improved angiography. Not only is an image quality improved, but time is also saved, since an operator is supported in a choice of the recording angles and a smaller number of recordings is required for an angiography of sufficient quality. Also an exposure of the patient to radiation, that is required for the computation of the virtual FFR value, is minimized.

In an embodiment there is provision for the assessment criterion to include a degree of a superimposition of at least one further body vessel segment or further segments of the body vessel on the body vessel segment or marked body vessel segment on the respective recording of the one or marked body vessel segment. A lower degree of superimposition is assessed that is better than a high degree of superimposition. The degree of superimposition or measure of superimposition may be determined such that, for each angulation or each recording angle from the three-dimensional reconstruction, a projection is created and the proportion of pixels is determined on which two or more of the corresponding body vessel segments are projected. The measurement is minimized. Precisely the one body vessel or the marked body vessel that is of interest for the angiography, for example because of the presence of a stenosis, is easy to see in the angiography and may be quantified precisely. A later segmentation of the image data is easier for the angiography, e.g. an assignment of pixels or voxels to the body vessel (or body vessel segment) or other structures.

In an embodiment, the assessment criterion includes a degree of a peripheral superimposition of at least one further body vessel segment with one another, with itself, or between a number of different further body vessel segments with one another on the respective recording of the one body vessel segment or the marked body vessel segment. A smaller degree of superimposition is assessed as better than a high degree of superimposition. Less account may be taken of the degree of the peripheral superimposition in the result of the assessment than of the degree of the superimposition for the one body vessel segment or the marked body vessel segment. The assessment criterion may include the degree of the superimposition as well as the degree of the peripheral superimposition. The marked body vessel segment or body vessel segment, in which for example the stenosis is present, may be captured with precision in the angiography, so that overall an optimal angulation or recording angle planning may be achieved for the computation of an angio FFR value for example.

In an embodiment, the assessment criterion includes an accessibility of the corresponding recording angle or the corresponding recording angles for the x-ray device. An inaccessible recording angle may not to be able to be selected for the creation of the three-dimensional angiography. A recording angle pair that may be accessed with a lower movement effort, e.g. for example with a smaller movement and/or in a shorter time, is assessed as better than a recording angle pair that may be accessed with a higher movement effort. For example, the x-ray device may include a C-arm x-ray device, and as such, an accessibility of a position by a C-arm of the x-ray device may be taken into account. The ability to access a particular position may be stored on the basis of tables in the x-ray device for example. An operating time and/or recording time is reduced and an operator is not led astray by supposedly advantageous angulations or recording angles that are not able to be realized at the x-ray device. The x-ray device is prevented in advance from moving to a less suitable substitute recording angle in the vicinity of the inaccessible recording angle and the accuracy of the angiography is improved.

In an embodiment, the recording angle is provided in a plane perpendicular, or essentially perpendicular, to the axis of rotation, to enclose a predetermined or predeterminable intermediate angle. The assessment criterion includes the intermediate angle. A recording angle pair with a greater intermediate angle is assessed as better than a recording angle pair with a smaller intermediate angle. The intermediate angle is the amount of the smaller differential angle between the recording angles and may thus only lie between 0° and 90°. The three-dimensional angiography from the two-dimensional first and the two-dimensional second recording from the first and second recording angle is improved in quality.

In another embodiment, the assessment criterion includes an expected radiation load on a patient for whose body vessel segment or marked body vessel segment the angiography will be created. A lower radiation load is assessed as better than a high radiation load. The radiation load to be expected may be stored in the form of a table for the different recording angles in the x-ray device or may be computed in accordance with a model. A patient's health may be protected or better preserved.

In a further embodiment, the assessment criterion includes an image quality of the recording to be expected, for example, a signal-to-noise ratio (SNR) to be expected and/or an image sharpness to be expected. A high image quality is assessed as better than a low image quality. The three-dimensional angiography is improved and accordingly follow-up computations, such as of the angio FFR value for example, may be determined with a higher precision.

In a further embodiment, the assessment criterion includes a position of a patient table of the x-ray device able to be changed for the recordings. A recording angle pair without a change or with a small change of the table position is assessed as better than a recording angle pair with a change or with a larger change of the table position. Since additional movements involve an additional inaccuracy or an additional computing effort in order to avoid a corresponding inaccuracy, taking account of any required change of table position in the assessment of the recording angle or of the recording angle pair is advantageous in order to provide an improved accuracy for the three-dimensional angiography.

Various different components or parts of the assessment criterion mentioned in the different forms of embodiment may in such cases also be taken into account jointly with one or more other components of the assessment criterion and be weighted differently. For example, a weighting may be used with the following criterion: a degree of the superimposition of at least one further body vessel segment on the body vessel segment, degree of the peripheral superimposition, accessibility of the corresponding recording angles or corresponding recording angle, intermediate angle between the recording angles, the radiation load on the patient to be expected, the image quality of the recording to be expected and the change in the position of the patient table for the recordings. A three-dimensional angiography is provided.

In a further embodiment the position of the patient table is defined for a recording angle pair in each case and, for example, for a body vessel segment or the marked body vessel segment to be located by the definition in an isocenter of the x-ray device. The change in the position of the table will be excluded from the outset as an additional parameter to be taken into account and the creation of the three-dimensional angiography is easier or the result is improved. The arrangement of the one body vessel segment or marked body vessel segment in an isocenter of the x-ray device is advantageous.

In a further embodiment, the intermediate angle enclosed by the recording angles in the plane perpendicular to the axis of rotation may amount to between 25° and 90°, for example, between 30° and 90°. The quality of the three-dimensional angiography achieves a predetermined minimum quality.

In another embodiment, the recording angle pair or the first and the second recording angle is selected automatically by the computing device of the x-ray device. As an alternative or in addition, a pre-selection is made automatically by the computing device of the x-ray device, so that a selection may be made by an operator from a reduced number of different recording angle pairs. The operator, for example, for the different recording angle pairs or recording angles, may be shown a result of the assessment. Many recording angles or recording angle pairs may be assessed and taken into account in a simple and rapid way, so that at the end, the best possible recording angle or the best possible recording angle pair may be selected and subsequently used for the creation of the three-dimensional angiography.

Embodiments relate to an x-ray device for a creation of a three-dimensional angiography of a body vessel segment or body vessel with a computing device, on which a three-dimensional reconstruction of the body vessel segment or body vessel is able to be provided. A center line through the body vessel segment is computed by the computing device. An axis of rotation may be laid through the center line. The three-dimensional reconstruction is registered by the computing device to the x-ray device. The computing device is further configured to evaluate the suitability of at least one recording angle pair with a first and a second recording angle for the creation of the three-dimensional angiography on the basis of an assessment criterion. The assessed recording angles are perpendicular to the axis of rotation in each case. The computing device is further configured to select or to pre-select one of the at least one recording angle pairs with one of the first and one of the second recording angles for creation of the three-dimensional angiography as a function of a result of the assessment.

DETAILED DESCRIPTION

Figure 1:
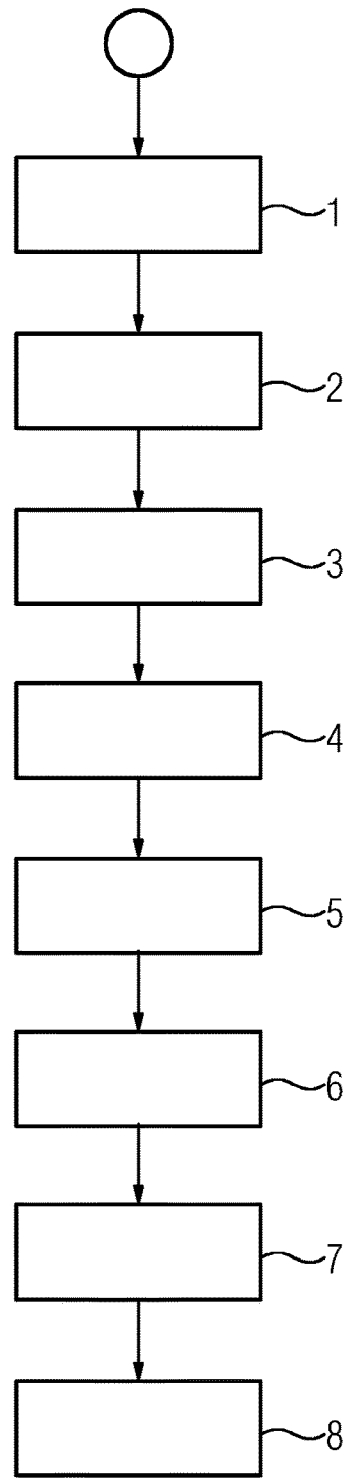
FIG. 1 depicts a schematic flow diagram for operating an x-ray device for a creation of a three-dimensional angiography according to an embodiment.
Figure 2:
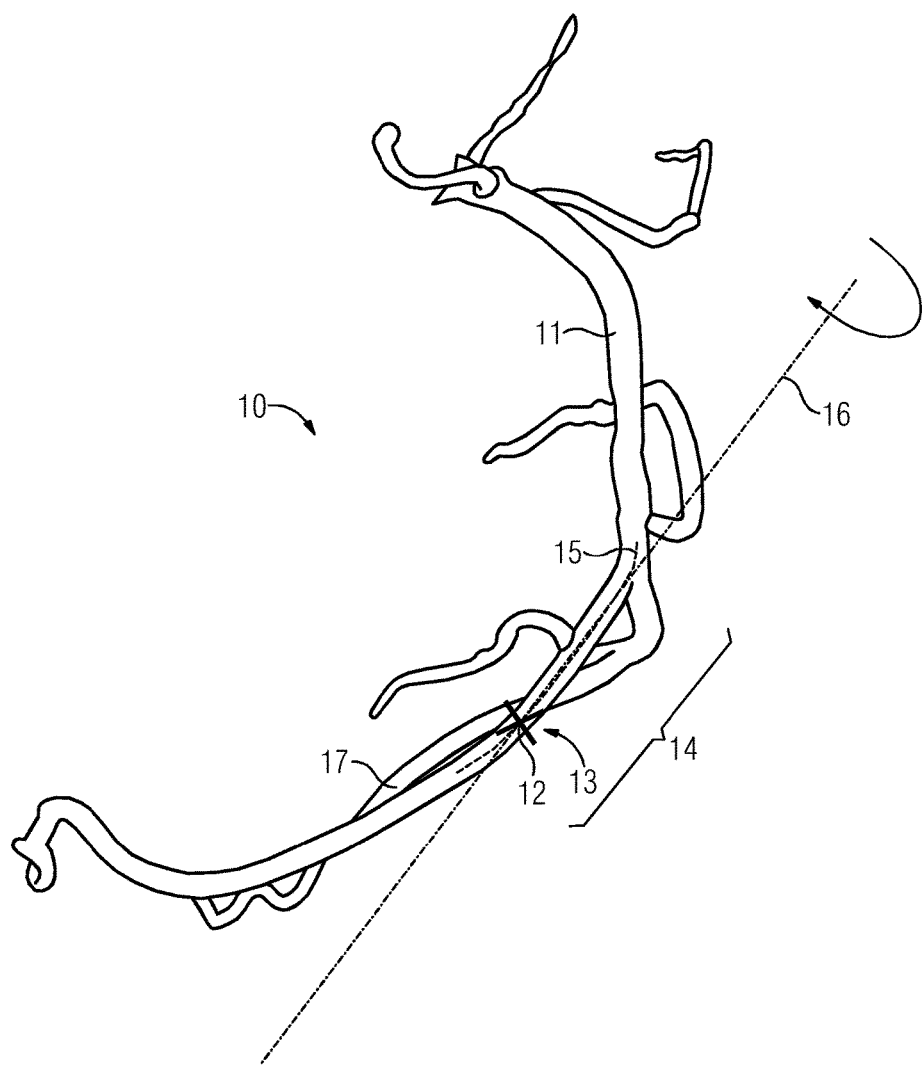
FIG. 2 depicts a diagram of a body vessel segment with a stenosis and an axis of rotation according to an embodiment.

FIG. 1 depicts a method for operating an x-ray device for a creation of a three-dimensional angiography of body vessel. FIG. 1 includes a provision 1 of a three-dimensional reconstruction 10 (also depicted in FIG. 2) of the body vessel 11 by another imaging device (e.g., a computed tomograph). FIG. 2 depicts a diagram of a body vessel segment. The three-dimensional reconstruction of the body vessel is provided to a computing device of the x-ray device, for example, in the form of a registration dataset yet to be registered with the x-ray device. A marking 2 of a body vessel segment of the body vessel in the three-dimensional reconstruction is done by an operator. The operator marks a body vessel segment 14 of the body vessel in which a stenosis 13 is present, for example. The computing device computes a computation 3 of a center line 15 through the marked body vessel segment. The center line may follow the course of the body vessel in the region of the stenosis. The computing devices lays a laying 4 of an axis of rotation 16 through the center line, so that the computing device may subsequently compute recording angles or angulations around the axis of rotation, which show the marked vessel segment in a longitudinal course.

A registration 5 of the registration dataset and thus of the three-dimensional reconstruction with a planning dataset of the body vessel recorded by the x-ray device for the creation of the three-dimensional angiography and thus with the x-ray device is provided, enabling the registration dataset. Features or information from the three-dimensional reconstruction may thereby be used for the creation of the three-dimensional angiography by the x-ray device. There may be a selection 7 of a suitable recording angle or a second suitable recording angle as a recording angle pair by the x-ray device.

An assessment 6 of the suitability of at least one recording angle pair with a first and a second recording angle (e.g., a plurality of such recording angle pairs) or of at least one first and/or at least one second recording angle, is provided for the creation of the three-dimensional angiography based on an assessment criterion by the computing device. The assessed recording angles are perpendicular in each case to the axis of rotation. In the example depicted, all possible recording angles perpendicular to the axis of rotation are assessed in order to establish the recording angle pair best suited for the three-dimensional angiography.

The assessment criterion, in the example depicted, includes a degree of a superimposition of at least one further body vessel segment of the body vessel on the marked body vessel segment on the respective recording of the marked body vessel segment. Since in the region of the stenosis a superimposition-free recording is important, in the present case, it is this assessment criterion that is given the greatest weight in a result of the assessment by comparison with the further components of the assessment criterion given below.

In the present example, the assessment criterion includes a degree of a peripheral superimposition between at least one further body vessel segment as well as an accessibility of the corresponding recording angle by the x-ray device. The recording angles or recording angle pairs that are poorly accessible or inaccessible are sorted out. The superimpositions for the further vessel segments, in which no stenosis is present, are minimized in the recordings.

There may be a selection 7 of an assessed recording angle pair of the three-dimensional angiography. The selection 7 is effected as a function of a result of the assessment, so that the recording angle pair with the best result will be selected. The selection 7 may be effected automatically. In the depicted example, the selection 7 is effected semi-automatically. There is first an automatic pre-selection, from which the one recording angle pair that is to be used for the creation of the three-dimensional angiography will then be selected by an operator.

The creation 8 of the three-dimensional angiography of the body vessel with the marked body vessel segment is created by the x-ray device by a recording from the first recording angle and the second recording angle of the selected recording angle pair in each case.

FIG. 2 depicts a diagram of a body vessel segment with a stenosis and an axis of rotation. The three-dimensional reconstruction 10 of the body vessel 11 in the example includes a stenosis 13 at a position 12. Accordingly, a body vessel segment 14 is marked in the present example by an operator. A center line 15 through the body vessel segment 14 is computed by a computing device of the x-ray device. An axis of rotation 16 is laid through the center line 15, to which the recording angles subsequently assessed by the computing device based on the assessment criterion are perpendicular. A further body vessel segment 17 that, as depicted, is located partly behind the body vessel segment 14 and may be overlaid in a recording with the body vessel segment 14.

The information from the three-dimensional reconstruction 10 is used for the creation 8 (FIG. 1) of the three-dimensional angiography and provides for an optimized three-dimensional angiography to be created.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating an x-ray device for creation of a three-dimensional angiography of a body vessel segment, the method comprising:

provided a three-dimensional reconstruction of the body vessel segment to a computing device of the x-ray device;

calculating a center line through the body vessel segment;

calculating, by the computing device, an axis of rotation through the center line;

registering the three-dimensional reconstruction with the x-ray device;

assessing, by the computing device, a suitability of at least one recording angle pair with a first recording angle and a second recording angle for the creation of the three-dimensional angiography based on an assessment criterion, wherein the assessed recording angles are perpendicular to the axis of rotation; and selecting one of the at least one evaluated recording angle pair for creation of the three-dimensional angiography as a function of a result of the evaluation.

2. The method of claim 1, wherein the assessment criterion comprises a degree of a superimposition of at least one further body vessel segment on the body vessel segment on the respective recording of the one body vessel segment, wherein a lower degree of superimposition is better than a higher degree of superimposition.

3. The method of claim 1, wherein the assessment criterion comprise a degree of a peripheral superimposition of at least one further body vessel segment with each other on the respective recording of the one body vessel segment, and a smaller degree of superimposition is evaluated as better than a high degree of superimposition, wherein the degree of the peripheral superimposition is taken into account less in the result of the evaluation than the degree of the superimposition for the one body vessel segment.

4. The method of claim 1, wherein the assessment criterion comprises an accessibility of the corresponding recording angle by the x-ray device, wherein a recording angle not able to be accessed by the x-ray device is not selected for creation of the three-dimensional angiography, wherein a recording angle pair accessible with a lower movement effort is evaluated as better than a recording angle pair accessible with a higher movement effort.

5. The method of claim 1, wherein the recording angles, in a plane perpendicular to the axis of rotation, enclose a predetermined intermediate angle and the assessment criterion comprise an intermediate angle, and a recording angle pair with a larger intermediate angle is assessed as better than a recording angle pair with a smaller intermediate angle.

6. The method of claim 1, wherein the assessment criterion comprises a radiation load to be expected for a patient, for whose body vessel segment the angiography is created, and a small radiation load is assessed as better than a high radiation load.

7. The method of claim 1, wherein the assessment criterion comprises an image quality of the recording to be expected, wherein a high image quality is assessed as better than a low image quality.

8. The method of claim 7, wherein the image quality of the recording to be expected includes a signal-to-noise ratio, an image sharpness to be expected, or the signal-to-noise ratio and the image sharpness to be expected.

9. The method of claim 1, wherein the assessment criterion comprises a position of a patient table of the x-ray device able to be changed for the recording, and a recording angle pair without a change or with a first change of the table position is assessed as better than a recording angle pair with a change or with a second, larger change of the table position.

10. The method of claim 9, wherein the table position of the patient table is defined in each case for the recording angle pair, and wherein the one body vessel segment is located in an isocenter of the x-ray device.

11. The method of claim 5, wherein the intermediate angle enclosed in the plane perpendicular to the axis of rotation by the recording angles amounts to between 25° and 90°.

12. The method of claim 1, wherein selecting is made automatically by the computing device of the x-ray device.

13. The method of claim 1, wherein the evaluated recording angles of are perpendicular to the axis of rotation.

14. An x-ray device for creation of a three-dimensional angiography of a body vessel segment, the x-ray device comprising:

a memory configured to store a three-dimensional reconstruction of the body vessel segment; and a computing device configured to calculate a center line through the body vessel segment and an axis of rotation through the center line;

wherein the three-dimensional reconstruction is registered with the x-ray device, and the computing device is further configured to assess a suitability of at least one recording angle pair with a first recording angle and a second recording angle for the creation of the three-dimensional angiography based on an assessment criterion;

wherein the assessed recording angles are perpendicular to the axis of rotation; and wherein one of the at least one recording angle pairs with one of the first and one of the second recording angles is selected for creation of the three-dimensional angiography as a function of a result of the assessment.

15. The x-ray device of claim 14, wherein the assessment criterion comprises a degree of a superimposition of at least one further body vessel segment on the body vessel segment on the respective recording of the one body vessel segment, wherein a lower degree of superimposition is better than a higher degree of superimposition.

16. The x-ray device of claim 14, wherein the assessment criterion comprises a degree of a peripheral superimposition of at least one further body vessel segment with each other on the respective recording of the one body vessel segment, and a smaller degree of superimposition is assessed as better than a high degree of superimposition, wherein the degree of the peripheral superimposition is used less in the result of the assessment than the degree of the superimposition for the one body vessel segment.

17. The x-ray device of claim 14, wherein the assessment criterion comprises an accessibility of the corresponding recording angle by the x-ray device, wherein a recording angle not able to be accessed by the x-ray device is not selected for creation of the three-dimensional angiography, wherein a recording angle pair accessible with a lower movement effort will be assessed as better than a recording angle pair accessible with a higher movement effort.

18. The x-ray device of claim 14, wherein the recording angles, in a plane perpendicular to the axis of rotation, enclose a predetermined intermediate angle, and the assessment criterion comprises an intermediate angle, and a recording angle pair with a larger intermediate angle is assessed as better than a recording angle pair with a smaller intermediate angle.

19. The x-ray device of claim 14, wherein the assessment criterion comprises a radiation load to be expected for a patient, for whose body vessel segment the angiography is created, and a small radiation load is assessed as better than a high radiation load.

20. The x-ray device of claim 14, wherein the assessment criterion comprises an image quality of the recording to be expected, a signal-to-noise ratio, or an image sharpness to be expected, wherein a high image quality is assessed as better than a low image quality.

* * * * *